(12) United States Patent
Galloway et al.

(10) Patent No.: US 7,282,059 B1
(45) Date of Patent: Oct. 16, 2007

(54) CONSTANT FORCE ACTUATOR FOR BLEEDING TIME TESTING DEVICE

(75) Inventors: Edward L. Galloway, Beaumont, TX (US); Eric Petersen, Beaumont, TX (US); Tipton Golias, Beaumont, TX (US)

(73) Assignee: Helena Laboratories, Beaumont, TX (US)

( * ) Notice: Subject to any disclaimer, the term of this patent is extended or adjusted under 35 U.S.C. 154(b) by 668 days.

(21) Appl. No.: 10/612,499

(22) Filed: Jul. 2, 2003

Related U.S. Application Data

(60) Provisional application No. 60/393,971, filed on Jul. 5, 2002.

(51) Int. Cl.
*A61B 17/14* (2006.01)
(52) U.S. Cl. ............. 606/182; 606/167; 606/185
(58) Field of Classification Search ............. 606/182, 606/181, 185, 167
See application file for complete search history.

(56) References Cited

U.S. PATENT DOCUMENTS

| | | | |
|---|---|---|---|
| 2,711,738 A * | 6/1955 | Kelly et al. ............. 606/182 |
| 3,760,809 A * | 9/1973 | Campbell, Jr. ............. 606/182 |
| 4,064,871 A | 12/1977 | Reno |
| 4,078,552 A * | 3/1978 | Chen et al. ............. 600/369 |
| 4,203,446 A * | 5/1980 | Hofert et al. ............. 606/182 |
| 4,462,405 A * | 7/1984 | Ehrlich ............. 606/182 |
| 4,628,929 A * | 12/1986 | Intengan et al. ............. 606/182 |
| 4,735,203 A * | 4/1988 | Ryder et al. ............. 606/182 |
| 5,031,619 A | 7/1991 | Pompei |
| 5,527,334 A * | 6/1996 | Kanner et al. ............. 606/182 |
| 5,662,672 A | 9/1997 | Pambianchi et al. |
| 5,733,300 A * | 3/1998 | Pambianchi et al. ......... 606/181 |
| 5,797,940 A * | 8/1998 | Mawhirt et al. ............. 606/167 |
| 6,042,595 A * | 3/2000 | Morita ............. 606/181 |
| 6,190,398 B1 * | 2/2001 | Schraga ............. 606/181 |

* cited by examiner

*Primary Examiner*—Darwin P. Erezo
(74) *Attorney, Agent, or Firm*—Egbert Law Offices

(57) ABSTRACT

A bleeding time testing system including a bleeding time tester having a cutting blade and a switch actuator, and a tripper affixed onto the body of the tester and cooperative with the switch actuator. The tripper includes a housing, a slide frame slidably interconnected to the housing and having a surface cooperative with the switch actuator, and an actuator button mounted on the housing and cooperative with the slide frame. The actuator button is positioned so as to cause the slide frame to move to the activated position when the actuator is moved downwardly. The actuator button is positioned directly above a centerline of the cutting blade of the tester.

11 Claims, 4 Drawing Sheets

CONSTANT FORCE ACTUATOR FOR BLEEDING TIME TESTING DEVICE

RELATED U.S. APPLICATIONS

The present application claims priority under 35 U.S.C. §119(e) from a parent application, U.S. Provisional Application Ser. No. 60/393,971 filed on Jul. 5, 2002 and entitled "Constant Force Actuator for Bleeding Time Testing Device" to the same inventors.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to medical devices useful in determining bleeding times. More particularly, the present invention relates to actuators for bleeding time testing devices. Furthermore, the present invention relates to actuators for bleeding time testing devices which apply a controlled load and a constant force during the cutting operation.

BACKGROUND OF THE INVENTION

In the medical field, it is a very common procedure, and often very necessary, to conduct a bleeding time test which measures the time required for the cessation of bleeding following a skin incision. This test is medically important because extended or prolonged bleeding time can be associated with, for example, a lack of or a great excess of platelets, abnormality of platelet function, coating of platelets by specific proteins or foreign materials or the action of certain drugs; e.g., aspirin.

Although the bleeding time test procedure was first described approximately ninety years ago, it did not receive general acceptance until the 1940's at which time the test's sensitivity was increased by making a skin incision on the forearm of the patient while maintaining a blood pressure cuff inflation to maintain venostasis at a standardized level. Using this procedure, a technologist simultaneously starts a stopwatch while making the incision. The emerging blood is then gently blotted every thirty seconds. The cessation of bleeding is defined as the time at which the blotting paper is no longer stained by the emerging blood. This amount of time is generally recorded to the nearest half minute.

Disposable bleeding time devices were first introduced in 1978 to facilitate automation and convenience. These devices improved the acceptance of the test by both the patient and the operator. However, the results were still subject to a variety of technical variables. Additionally, these devices were significantly more expensive than previous methods. This hindered the acceptance of such devices in many countries around the world. Importantly, different disposable devices evolved over time which were functionally quite dissimilar so that the results were not comparable. Thus, standardization remained an elusive goal in bleeding time testing.

An important bleeding time testing device is known as the TRIPLETT (TM) bleeding time testing device. This was named after the noted physician in blood coagulation and hematopathology, Dr. Douglas Triplett. This device is presently manufactured and sold by Helena Laboratories of Beaumont, Tex. This device met the goal of global standardization in bleeding time testing and utilizes advanced technology at a universally affordable price. This was a product that provided a new level of value to automated, disposable bleeding time devices. This TRIPLETT (TM) bleeding time testing device was designed to be user and patient friendly, virtually painless, and to mimic the incision motion of the original bleeding time method. The device makes a standardized surgical incision one millimeter deep by five millimeters long for accurate sensitive bleeding time testing. The blade automatically retracts after incisions so as to ensure safety. The device includes a large contact surface that distributes the downward force over a wider area of skin so as to reduce the potential for deep non-standardized cuts. This device is presently subject to patent protection under U.S. Pat. Nos. 5,662,672 and 5,733,300.

Various other U.S. patents have issued relating to such bleeding time testing devices. For example, U.S. Pat. No. 4,064,871, issued on Dec. 27, 1977 to W. J. Reno, teaches a bleeding time testing device that includes a housing having a surface with a slot defining a longitudinal opening into the housing. A blade is mounted within the housing for movement of the blade tip through and along the slot. Biasing springs are provided within the housing to urge the blade through the slot a predetermined distance and along the slot for a predetermined length to control the depth and length of an incision produced with the device. A trigger is provided to initiate movement of the blade along with a safety pin to prevent the inadvertent activation of the device.

U.S. Pat. No. 4,628,929, issued on Dec. 16, 1986 to Intengan et al., describes another type of retractable bleeding time testing device. This device includes a housing, a hammer mechanism pivotally positioned within the housing and having a cam surface, and a self-retracting shuttle supported within the housing and including a cam follower surface. The shuttle is operative to travel in a vertical direction by the movement of the cam surface along the cam follower surface and the force exerted on the shuttle by a first spring extending from the shuttle. A cutting blade is secured to the shuttle and is operative to move out of the housing to make the incision and then to self-retract into the housing. A second spring is operative to exert a force on the hammer to cause it to move along the cam follower surface and to cause the shuttle to travel downwardly thus causing the blade to travel out of the housing to make the incision. The second spring is also operative to move into a locked position to secure the blade within the housing after the blade has retracted back into the housing.

U.S. Pat. No. 5,031,619, issued on Jul. 16, 1991, to F. Pompei, describes a method for determining bleeding time which includes a cutting assembly and a member for providing a compensation factor as a function of the temperature of the patient. The cutting assembly provides an incision of predetermined dimensions for external bleeding therethrough. The compensation member measures temperature of the patient throughout the period of external bleeding and provides a compensation factor as a function of the sensed temperature.

One of the problems associated with the use of the TRIPLETT (TM) device is that the force applied to actuate the device is off-center from the location at which the blade emerges from the cutting surface. As such, variations of pressures applied to the device can occur. As a result, the bleeding time testing can have a lack of consistent testing.

Angular deflections of the cutting surface can also occur by the off-center application of pressure to the actuator of such cutting device. As such, a need has developed for a device for actuating such bleeding time testing devices such that the pressure of actuation will be directly above the location of the incision.

It is an object of the present invention to provide an actuator for a bleeding time testing device which minimizes the variations between operators and the techniques used.

It is another object of the present invention to provide a bleeding time testing device which provides more consistent cutting action.

It is another object of the present invention to provide an actuator for a bleeding time testing device which removes any pressure variations during the incision process.

It is another object of the present invention to provide an actuator for a bleeding time testing device that has a tactile feedback to notify the operator when the actuation has occurred.

It is a further object of the present invention to provide an actuator for a bleeding time testing device which will remain locked down after the actuation so as to assure that the device cannot be reused.

It is a further object of the present invention to provide an actuator for a bleeding time testing device which prevents accidental premature actuation.

It is still a further object of the present invention to provide an actuator for a bleeding time testing device which allows different pressures to be applied to the actuator button by changing the actuator spring.

These and other objects and advantages of the present invention will become apparent from a reading of the attached specification.

BRIEF SUMMARY OF THE INVENTION

The present invention is an actuator for (i.e. tripper) a bleeding time testing device in which a constant force device is applied to the bleeding time testing device. In the present invention, the bleeding time testing device includes a body having a bottom surface through which a cutting blade emerges so as to carry out the incision. The body includes a switch actuator which extends outwardly of the top surface of the testing device body. This switch actuator is movable between a pre-actuating position and an actuating position. A safety tab is removably positioned against the switch actuator so as to retain the switch actuator in its pre-actuating position. The safety tab must be removed so as to enable the testing device to be actuated by moving the switch actuator from the pre-actuating position to the actuating position. The cutting blade is cooperative with the switch actuator to move outwardly of the bottom surface of the body of the testing device when the switch actuator is moved to the actuating position.

The present invention includes a constant force device having a housing that can be mounted onto the bleeding time testing device. The housing is arranged generally parallel to the bottom surface of the bleeding time testing device. A suitable spring clip can be provided on the housing so as to allow the actuator housing to be affixed to the body of the bleeding time testing device.

In the tripper of the present invention, a slide frame is mounted on the housing so as to be in slidable relationship to the housing. This slide frame is movable between a pre-activated position and an activated position. In the pre-activated position, the slide frame will have a surface which resides against the switch actuator of the bleeding time testing device in the pre-activated position. The slide frame has an inverted U-shaped slot formed on the sides of the frame so as to open at a bottom edge of the frame. A spring is mounted so as to be cooperative with the slide frame so as to urge the slide frame toward the activated position.

An actuator button is slidably mounted on the housing so as to be slidable in a direction transverse to the plane of the bottom surface of the bleeding time testing device. This actuator button is movable between a pre-activated position and an activating position. The actuator button includes a top surface having a pair of legs extending downwardly therefrom. This pair of legs is positioned on the outer surfaces of the sides of the slide frame. A pin will extend inwardly from each of the legs so as to be received within the inverted U-shaped slot of the slide frame when the actuator button is in the pre-activated position. These pins are movable so as to be free of the U-shaped slot and move into a slot formed in the housing below the slide frame when the button is pushed to the activating position. As a result, the spring associated with the slide frame will urge the slide frame to move in a horizontal direction parallel to the bottom surface of the bleeding time testing device and thereby move the switch actuator of the bleeding time testing device from the pre-actuating position to the actuating position. The actuator button is positioned directly above the centerline of the cutting blade during the incision procedure.

A support structure is provided over the housing. The housing includes a pair of channels on opposite sides thereof. The sides of the slide frame slide in these channels. This support structure has a top surface with a pair of legs connected to the housing. The legs of the support structure extend over the channels and over the sides of the slide frame. The sides of the slide frame will extend between the legs of the support and the legs of the actuator button. A spring is interposed between the top surface of the housing and the underside of the top surface of the actuator button so as to urge the actuator button into the pre-activated position.

DETAILED DESCRIPTION OF THE INVENTION

Figure 1:
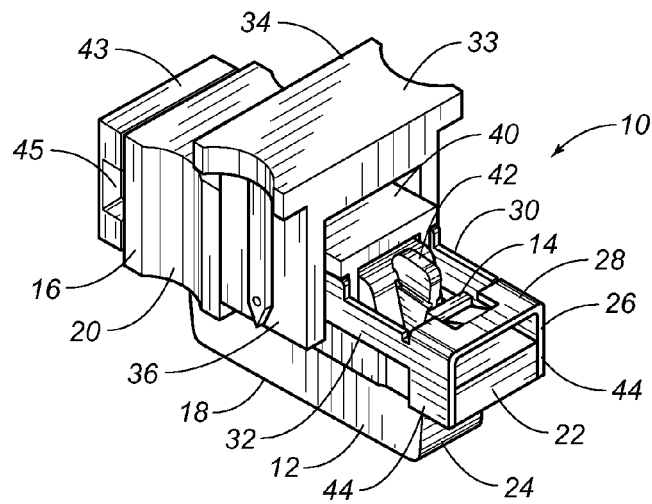
FIG. 1 is a perspective view of the bleeding time testing device and tripper in accordance with the preferred embodiment of the present invention.

Referring to FIG. 1, there is shown the tripper 10 for the bleeding time testing device 12 in accordance with the teachings of the present invention. The tripper 10 is a constant force device for the actuating of the switch actuator 14 extending outwardly from the top surface of the bleeding time testing device 12. The tripper 10 includes a housing 16 that is mounted over the top surface of the bleeding time testing device 12 in generally parallel relationship to the bottom surface 18 of the bleeding time testing device 12. The housing 16 includes a support structure 20 for securing the housing 16 to the body of the bleeding time testing device 12. The housing 16 will extend around the periphery of the bleeding time testing device 12 and will have a forward end 22 extending outwardly beyond the forward end 24 of the bleeding time testing device 12.

A slide frame 26 is in slidable relationship with the housing 16. In FIG. 1, slide frame 26 is shown in its pre-activated position. The slide frame 26 includes an abutment member 28 that is juxtaposed against the switch actuator 14 when the switch actuator 14 is in its pre-actuating position (as shown in FIG. 1). The slide frame 26 also has sides 30 and 32 which extend from the abutment section 28 and along the housing 16.

An actuator button 33 is mounted onto the housing 16 of tripper 10 and is movable in a direction transverse to the plane of the bottom surface 18 of the bleeding time testing device 12. The actuator button 33 includes a top surface 34, a first leg 36 and a second leg 38. A surface 40 of the housing 16 is positioned between the legs 36 and 38 of the actuator button 33. The sides 30 and 32 of the slide frame 26 are mounted between the legs 36 and 38 of the actuator button 33. The support structure 20 is positioned rearwardly of the actuator button 33 and over the slide frame 26. The support structure 20 will also include a suitable spring (not shown) for resiliently retaining the tripper 10 onto the body of the bleeding time testing device 12. An end cap 43 is affixed to the end of the end 45 of the slide frame 26. The end cap 43 will reside against the end surface of the support structure 20 opposite the actuator button 33.

In FIG. 1, it can be seen that a safety tab 42 is positioned against the switch actuator 14 of the bleeding time testing device 12. The safety tab 42 will prevent an inadvertent movement of the switch actuator 14 from the pre-actuating position to the actuating position.

In FIG. 1, it can also be seen that the slide frame 26 has a pair of fingers 44 extending downwardly from the respective sides 30 and 32 of the slide frame 26. Fingers 44 are positioned on the sides of the forward end of the housing 16 so as to slide therealong when the slide frame 26 moves from its pre-activated position to its activated position.

Figure 2:
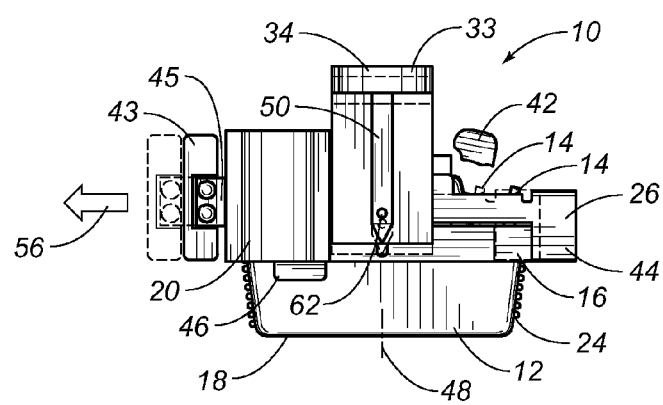
FIG. 2 is a side elevational view showing the tripper and the bleeding time testing device with the pre-activated position shown in solid lines and the activated position shown in broken lines.

FIG. 2 shows the operation of the tipper 10 of the present invention. Initially, in FIG. 2, it can be seen that the support structure 20 of the housing 16 includes a spring clip 46 which secures the tripper 10 onto the body of the bleeding time testing device 12. The bleeding time testing device 12 has bottom surface 18 with a cutting action centerline 48 illustrated in broken line fashion. An arrow 50 is illustrated on the actuator button 33 so as to show that the travel of the actuator button 33 is aligned with the centerline 48 of the cutting blade associated with the bleeding time testing device 12. Also, in FIG. 2, the broken lines show the movement of the actuator button 33 and the slide frame 26 from the pre-activated position to the activated position.

Initially in FIG. 2, it can be seen that the fingers 44 of the slide frame 26 are disposed away from the forward end 24 of the bleeding time testing device 12. Similarly, the actuator button 33 is shown in its uppermost position. The switch pin actuator 14 is illustrated in its pre-actuating position.

To actuate the present invention, it is initially necessary to remove the safety tab 42 from its position against the switch actuator 14. This is the first safety measure to prevent accidental release of the blade of the bleeding time testing device 12. Once the safety tab 42 is removed, the tripper 10 is ready for use. A downward pressure can be applied to the top surface 34 of the actuator button 33. As a result, the actuator button 33 will overcome the resistance of the spring 52 so as to move downwardly. As will be described hereinafter, a pin will extend inwardly from each of the legs 36 and 38 so as to engage an inverted U-shaped slot formed on the sides 30 and 32 of the slide frame 26. When these pins slide downwardly so as to be released from this inverted U-shaped slot, the slide frame 26 will be free for movement. A spring element located at the rear of the tripper 10 will apply a force to the slide frame 26 so as to move the slide frame 26 in the direction of arrow 56 until the fingers 44 reach the stop formed on the forward end 22 of the housing 16. When this movement occurs, the abutment member 28 will cause the switch actuator 14 to move from the position illustrated in solid lines in FIG. 2 to the actuating position shown in broken lines in FIG. 2. As a result, the cutting blade associated with the bleeding time testing device 12 will be suitably actuated so as to create the incision for the measurement of bleeding time.

Figure 3:
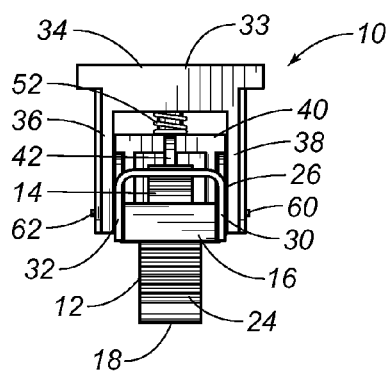
FIG. 3 is an end view of the tripper as placed upon the bleeding time testing device of the present invention.

In FIG. 3, it can be seen that the forward surface 24 of the bleeding time testing device 12 supports the tripper 10 thereon. The tripper 10 includes the housing 16, the slide frame 26 and the actuator button 33. The trigger 10 is mounted to the top surface of the bleeding time testing device 12 in generally parallel relationship to the bottom surface 18.

Importantly, in FIG. 3, it can be seen that the surface 40 of the housing 16 is located between the legs 36 and 38 of the actuator button 33. Legs 36 and 38 extend downwardly from the top surface 34 of actuator button 33. Pins 60 and 62 extend inwardly from the legs 38 and 36, respectively, so as to engage the inverted U-shaped slot formed on the respective sides 30 and 32 of the slide frame 26. A spring 52 is interposed between the surface 40 of and the underside of the top surface 34 of actuator button 33. The surface 40 is shown as having legs extending downwardly therefrom.

In FIG. 3, when the actuator button 33 is pressed downwardly so as to overcome the resistance of spring 52, the pins 60 and 62 will be released from the inverted U-shaped slots opening at the bottom of the sides 30 and 32 of slide frame 26. As a result, the spring 54 in FIG. 4 will resiliently urge the slide frame 26 rearwardly so as to push the switch actuator 14 to its actuating position. In FIG. 3, the safety tab 42 is illustrated as positioned behind the switch actuator 14.

Figure 4:
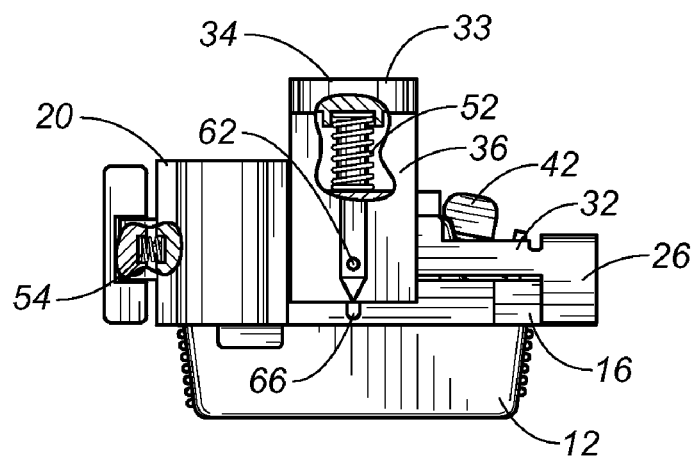
FIG. 4 is a side elevational view of the bleeding time testing device and tripper of the present invention illustrating, in broken away fashion, the location of the springs associated with the actuator button and with the slide frame.

In FIG. 4, the actuator button 33 is illustrated in its uppermost position. The pin 62 extends through the leg 36 of the actuator button 33. Spring 52 is shown as exerting a fore onto the underside of the top surface 34 of the actuator button 33. The pin 62 is illustrated as engaged with the inverted U-shaped slot formed on the side 32 of the slide frame 26. Another U-shaped slot 66 will be formed on the housing 16 so as to be generally aligned with the inverted U-shaped slot on the side 32 of slide frame 26. When the force is applied to the top surface of actuator button 33, the pin 62 will move downwardly and outwardly from the inverted U-shaped slot and into the slot 66 formed on the housing 16. If the safety tab 42 has been properly removed, then the slide frame 26 will move rapidly rearwardly because of the action of the spring 54 located at the back of the support structure or mounting section 20 of housing 16.

Figure 5:
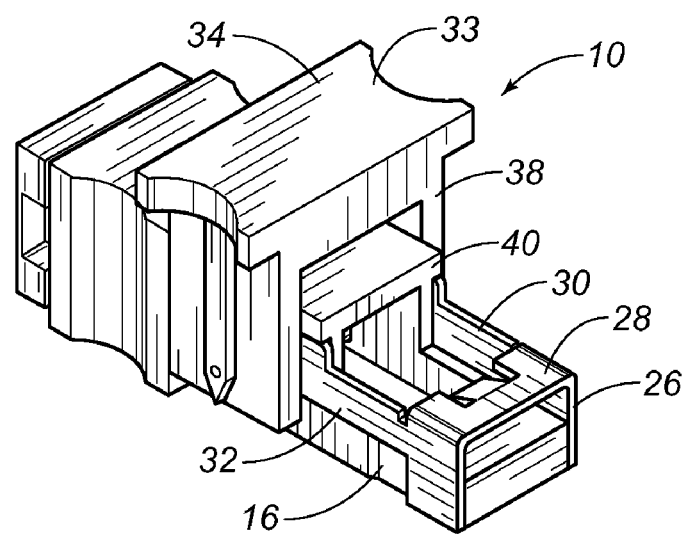
FIG. 5 is an isolated perspective view showing the tripper of the present invention.

FIG. 5 shows that the tripper 10 is separable from the bleeding time testing device 12. FIG. 5 shows that the slide frame 26 has abutment section 28 positioned at the forward end of the slide frame 26. Sides 30 and 32 are slidably mounted above the housing 16.

Figure 6:
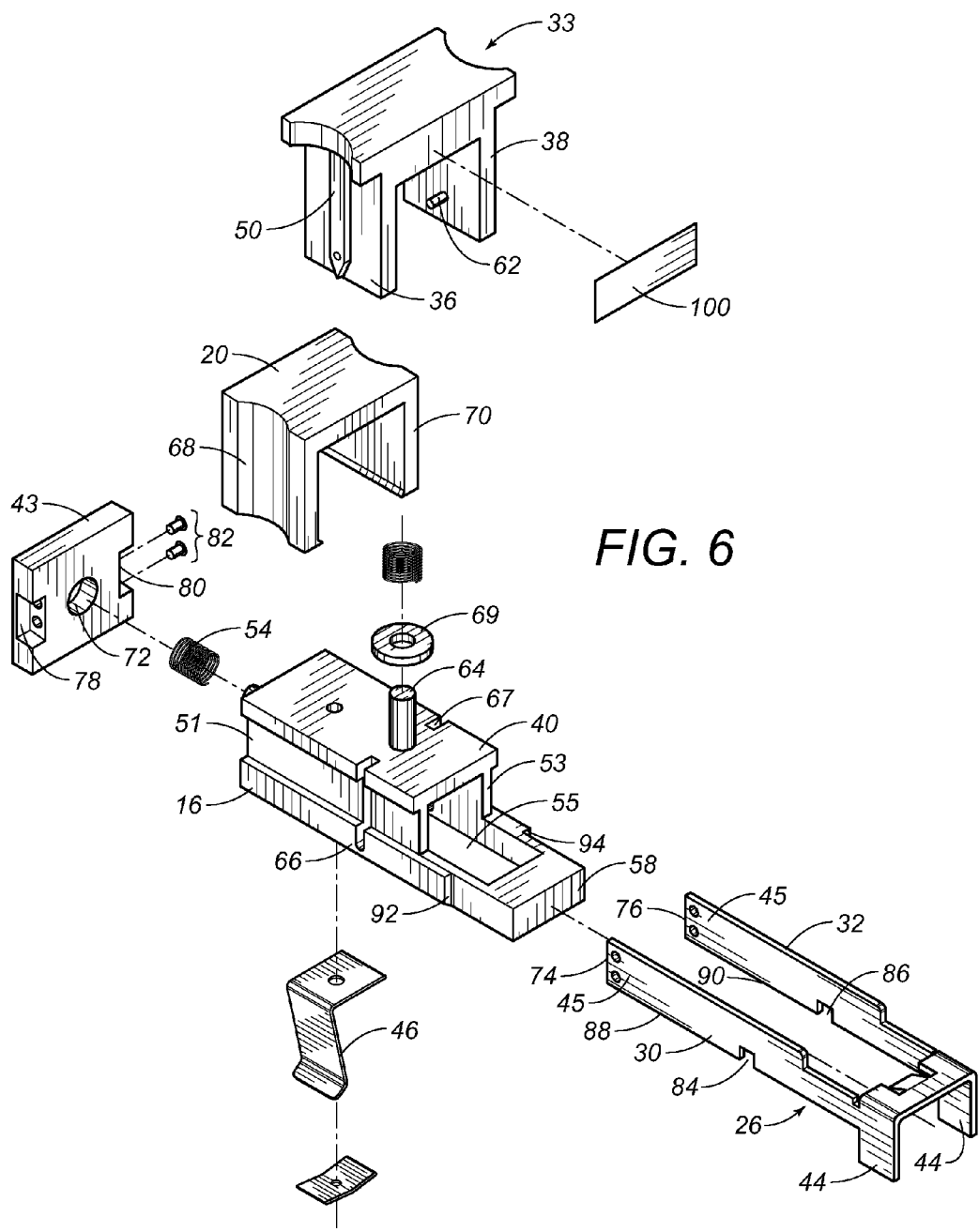
FIG. 6 is an exploded view in perspective of the tripper of the present invention.

FIG. 6 shows an exploded view of the tripper 10 of the present invention. In particular, in FIG. 6, it can be seen that the housing 16 has a pair of channels 51 and 53 formed on opposite sides thereof. The sides 30 and 32 of slide frame 26 will be slidably received within the channels 51 and 53. The housing 16 includes an interior opening 55 suitable for receiving the upper surface of the bleeding time testing device 12 therein. Cross member 58 will extend across a forward surface of the bleeding time testing device 12.

The housing 16 also includes a pair of slots 66 and 67 extending transversely there across. Slots 66 and 67 will be suitable for receiving the pins 60 and 62 which extend inwardly from the respective legs 36 and 38 of the actuator button 33. The top surface 40 of the housing 16 includes a locator pin 64 extending upwardly therefrom. Locator pin 64 provides an area onto which a washer 69 and spring 52 can be received. As such, the resilient spring 52 will exert a force upon the underside of the top surface 34 of the actuator button 33. The support structure 20 is illustrated as having separate legs 68 and 70 extending downwardly therefrom. Legs 68 and 70 will reside over the respective channels 51 and 53. The sides 30 and 32 of the slide frame 26 will reside between the inner surfaces of the leg 68 and 70 and the inner surfaces of the channels 51 and 53, respectively.

Another spring element 54 is positioned against the back end of the housing 16. Spring element 54 will have an end received within an orifice 72 formed on end cap 43. The ends 74 and 76 of the sides 30 and 32 of slide frame 26 will be affixed within cut out areas 78 and 80 formed on the end cap 43. Suitable pins 82 serve to secure the ends 74 and 76 into the cut out areas 78 and 80 of end cap 43.

In FIG. 6, it can be seen that the slide frame 26 has inverted U-shaped slots 84 and 86 formed therein. Inverted U-shaped slots 84 and 86 open along the bottom edges 88 and 90 of the respective sides 30 and 32. In normal use, the pins 60 and 62 extending inwardly from the legs 36 and 38 of the actuator button 33 will engage the inverted U-shaped slots 84 and 86 when in the pre-activated position. When the actuator button 33 is pressed downwardly, the pins 60 and 62 wilt move from the slots 84 and 86 and along the slots 66 and 67 of housing 16. As a result, the slide frame 26 will be released so as to move to its activated position. The abutment section 28 of the slide frame 26 will push on the switch actuator 14 of the bleeding time testing device.

The slide frame 26 also includes fingers 44 extending downwardly therefrom. Fingers 44 will contact shoulders 92 and 94 when the slide frame 26 is activated. As such, shoulders 92 and 94 will serve as a stop to the movement of the slide frame 26.

A resilient mounting spring 46 is illustrated as suitable for securing onto the hole 98 on the top surface 40 of the housing 16. The spring clip 46 has a portion which extends downwardly so as to exert a resilient force against the side of the body of the bleeding time testing device 12. The actuator button 33 has a name plate 100 suitable for attaching to a forward surface thereof.

Figure 7:
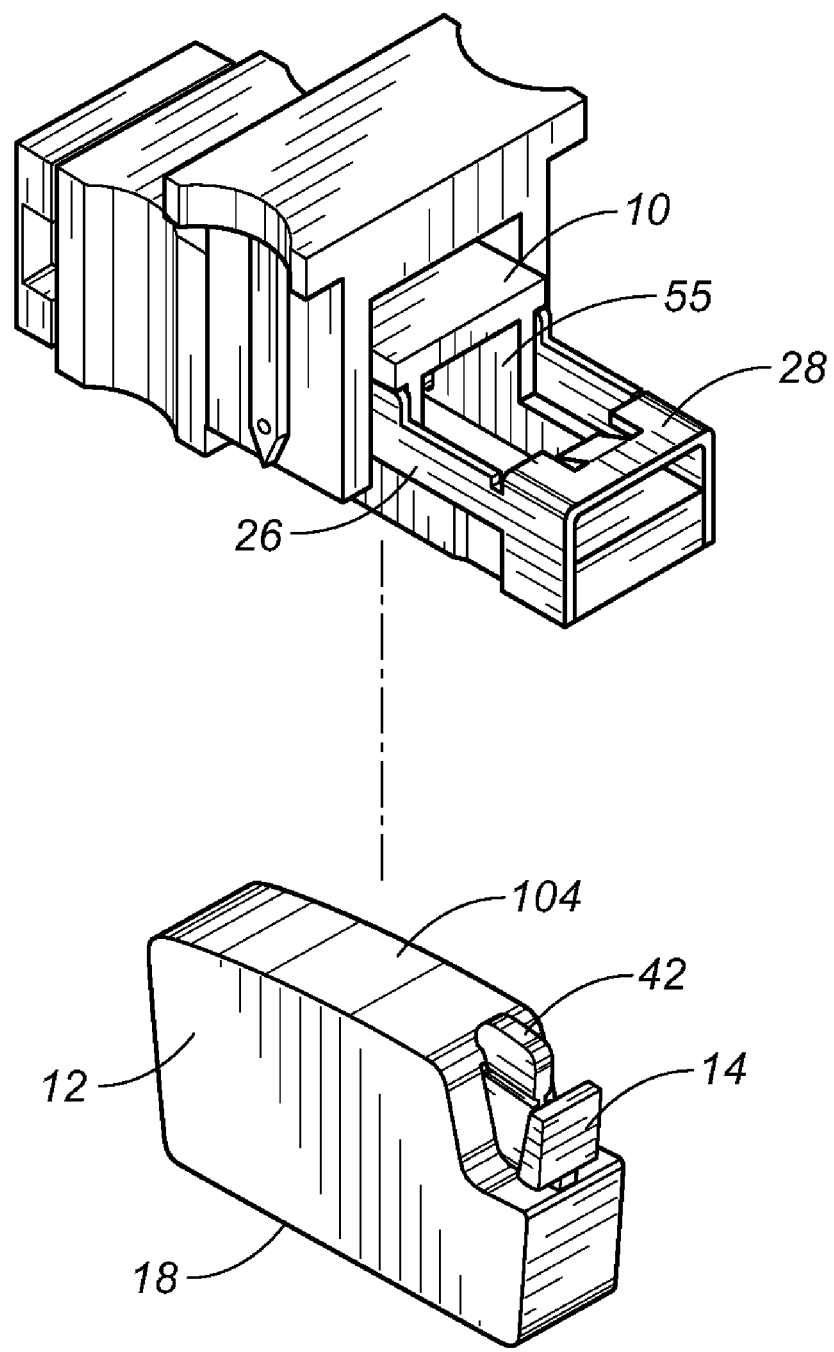
FIG. 7 is an exploded view showing the tripper and the bleeding time testing device of the present invention.

FIG. 7 shows an exploded perspective view in which the bleeding time testing device 12 is illustrated as being in a proper position for receipt within the interior opening or receptacle area 55 of the tripper 10. The bleeding time testing device 12 has a generally planar bottom surface 18 and a top surface 104. The switch actuator 14 extends outwardly of the top surface 104. Safety tab 42 is interposed between the body of the bleeding time testing device 12 and an inner surface of the switch actuator 14.

As can be seen in FIG. 7, the bleeding time testing device 12 can be placed within receptacle area 55 so that the switch actuator 14 will generally abut the abutment section 28 of the slide frame 26. When the safety tab 42 is removed, the system of the present invention will be ready for operation.

The tripper 10 of the present invention controls the force applied when the bleeding time testing device 12 is used for routine coagulation testing. When the force is controlled, the cutting action of the cutting blade will be more consistent and should minimize variations between operators and techniques employed. The tripper of the present invention has a controlled load which must be overcome in order for the device to activate and perform the incision. The controlled load will ensure that the same force is applied to the incision location (prior to the actual incision) in order to minimize the variations of operator techniques. The tripper 10 of the present invention is positioned over the desired cutting location. The force applied to the actuator button 33 travels directly downwardly at the centerline of the cutting blade position. The slide frame 26 of the actuator will travel a fixed distance so that the razor slide will be released. Once the razor slide is released, the razor slide will travel in a horizontal direction and automatically administer the incision.

The present invention controls the applied load at the incision site in order to remove any pressure variations during the incision process. The tripper 10 of the present invention provides tactile feedback to the operator when the actuation has occurred. The slide frame 26 of the tripper 10 remains locked down after actuation so as to ensure that the device cannot be reused. The various safety devices associated with the present invention serve to reduce any occurrences of accidental premature actuation. If necessary, the springs 52 and 54 can be replaced by other springs so as to allow for changing the pressures applied by the springs associated with the present device.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

We claim:

1. A bleeding time testing system comprising:
   a bleeding time tester comprising:
      a body having a top surface and a bottom surface;
      a cutting blade positioned in said body and movable between a first position within said body and a second position extending outwardly of said bottom surface of said body; and
      a switch actuator positioned so as to extend outwardly of said body, said switch actuator being movable between a pre-actuating position and an actuating position, said switch actuator cooperative with said cutting blade so as to move said cutting blade from said first position to said second position when said switch actuator is in said actuating position; and
   a tripper affixed onto said body of said bleeding time tester and cooperative with said switch actuator, said tripper comprising:
      a housing mounted onto said body;
      a slide frame slidably interconnected to said housing, said slide frame having a surface cooperative with said switch actuator of said bleeding time tester, said slide frame movable between a pre-activated position and an activated position, said slide frame extending in parallel relation to said bottom surface of said body; and an actuator button mounted on said housing and cooperative with said slide frame, said actuator button movable between a pre-activating position and an activating position, said actuator button causing said slide frame to move in parallel relation to said bottom surface of said body to said activated position when said actuator button is moved to said activating position, said slide frame having an inverted U-shaped slot formed on a side thereof, said actuator button having a pin extending inwardly therefrom in parallel relation to said bottom surface of said body, said pin received within said slot when said slide frame is in said pre-activating position, said pin movable out of said slot so as to cause said slide frame to move to said activating position.

2. The system of claim 1, said actuator button positioned directed above a centerline of said cutting blade when said blade is in said second position.

3. The system of claim 1, said bleeding time tester further comprising:

a safety tab removably positioned against said switch actuator so as to retain said switch actuator in said pre-actuating position.

4. The system of claim 1, said housing having a slot aligned with said inverted U-shaped slot of said slide frame, said pin received in and slidable along said slot of said housing.

5. A bleeding time testing system comprising:

a bleeding time tester comprising:
 a body having a top surface and a bottom surface;
 a cutting blade positioned in said body and movable between a first position within said body and a second position extending outwardly of said bottom surface of said body; and
 a switch actuator positioned so as to extend outwardly of said body, said switch actuator being movable between a pre-actuating position and an actuating position, said switch actuator cooperative with said cutting blade so as to move said cutting blade from said first position to said second position when said switch actuator is in said actuating position; and a tripper affixed onto said body of said bleeding time tester and cooperative with said switch actuator, said tripper comprising:
 a housing mounted onto said body;
 a slide frame slidably interconnected to said housing, said slide frame having a surface cooperative with said switch actuator of said bleeding time tester, said slide frame movable between a pre-activated position and an activated position, said slide frame extending in parallel relation to said bottom surface of said body;

an actuator button mounted on said housing and cooperative with said slide frame, said actuator button movable between a pre-activating position and an activating position, said actuator button causing said slide frame to move in parallel relation to said bottom surface of said body to said activated position when said actuator button is moved to said activating position; and a spring means interposed between said housing and a surface of said slide frame, said spring means for resilient urging said slide frame toward said activating position.

6. A bleeding time testing system comprising:

a bleeding time tester comprising:
 a body having a top surface and a bottom surface;
 a cutting blade positioned in said body and movable between a first position within said body and a second position extending outwardly of said bottom surface of said body; and
 a switch actuator positioned so as to extend outwardly of said body, said switch actuator being movable between a pre-actuating position and an actuating position, said switch actuator cooperative with said cutting blade so as to move said cutting blade from said first position to said second position when said switch actuator is in said actuating position; and a tripper affixed onto said body of said bleeding time tester and cooperative with said switch actuator, said tripper comprising:
 a housing mounted onto said body;
 a slide frame slidably interconnected to said housing, said slide frame having a surface cooperative with said switch actuator of said bleeding time tester, said slide frame movable between a pre-activated position and an activated position, said slide frame extending in parallel relation to said bottom surface of said body; and
 an actuator button mounted on said housing and cooperative with said slide frame, said actuator button movable between a pre-activating position and an activating position, said actuator button causing said slide frame to move in parallel relation to said bottom surface of said body to said activated position when said actuator button is moved to said activating position, said actuator button being slidable transverse to said bottom surface of said body, said actuator button movable downwardly so as to move to said activating position.

7. A bleeding time testing system comprising:

a bleeding time tester comprising:
 a body having a top surface and a bottom surface;
 a cutting blade positioned in said body and movable between a first position within said body and a second position extending outwardly of said bottom surface of said body; and
 a switch actuator positioned so as to extend outwardly of said body, said switch actuator being movable between a pre-actuating position and an actuating position, said switch actuator cooperative with said cutting blade so as to move said cutting blade from said first position to said second position when said switch actuator is in said actuating position; and a tripper affixed onto said body of said bleeding time tester and cooperative with said switch actuator, said tripper comprising:
 a housing mounted onto said body;
 a slide frame slidably interconnected to said housing, said slide frame having a surface cooperative with said switch actuator of said bleeding time tester, said slide frame movable between a pre-activated position and an activated position, said slide frame extending in parallel relation to said bottom surface of said body; and
 an actuator button mounted on said housing and cooperative with said slide frame, said actuator button movable between a pre-activating position and an activating position, said actuator button causing said slide frame to move in parallel relation to said bottom surface of said body to said activated position when said actuator button is moved to said activating position, said actuator button having a top surface and a pair of legs extending downwardly therefrom, said slide frame extending through and between said pair of legs.

8. The system of claim 7, said tripper further comprising:
a spring interposed between a surface of said housing and in contact with an underside of said top surface of said actuator button, said spring resiliently urging said actuator button to said pre-activating position.

9. The system of claim 7, said slide frame comprising:
a first side;
a second side extending in generally parallel relation to said first side; and
an abutment section affixed to an end of said first and second sides, said abutment section having a surface contacting said switch actuator.

10. The system of claim 7, said housing having a first channel on one side thereof and a second channel on an opposite side thereof, said first side of said slide frame being slidable in said first channel, said second side of said slide frame being slidable in said second channel.

11. The system of claim 9, each of said first and second sides of said slide frame having an inverted U-shaped slot formed therein, each of said pair of legs of said actuator button having a pin extending inwardly therefrom, the pin engaging the inverted U-shaped slot when said actuator button is in said pre-activating position.

\* \* \* \* \*